US007198787B2

(12) United States Patent
Fodstad et al.

(10) Patent No.: US 7,198,787 B2
(45) Date of Patent: Apr. 3, 2007

(54) METHOD OF KILLING TARGET CELLS IN HARVESTED CELL POPULATIONS WITH ONE OR MORE IMMUNO-TOXINS

(75) Inventors: Oystein Fodstad, Oslo (NO); Gunnar Kvalbeim, Oslo (NO); Meng yu Wang, Oslo (NO); Olav Engebraten, Lorenskog (NO); Siri Juell, Lommedalen (NO)

(73) Assignee: Oystein Fodstad, Oslo (NO)

( * ) Notice: Subject to any disclaimer, the term of this patent is extended or adjusted under 35 U.S.C. 154(b) by 375 days.

(21) Appl. No.: 09/125,751

(22) PCT Filed: Mar. 12, 1997

(86) PCT No.: PCT/NO97/00074

§ 371 (c)(1),
(2), (4) Date: Oct. 30, 1998

(87) PCT Pub. No.: WO97/33611

PCT Pub. Date: Sep. 18, 1997

(65) Prior Publication Data

US 2002/0151689 A1 Oct. 17, 2002

(30) Foreign Application Priority Data

Mar. 13, 1996 (NO) .............................................. 961031

(51) Int. Cl.
*A61K 39/395* (2006.01)
*A61K 39/40* (2006.01)
*G01N 33/574* (2006.01)

(52) U.S. Cl. .................................. 424/130.1; 424/131.1; 424/134.1; 424/137.1; 424/138.1; 424/141.1; 424/143.1; 424/152.1; 424/155.1; 424/156.1; 435/7.1; 435/7.23

(58) Field of Classification Search ................. 536/231; 435/4, 6, 7.1, 7.23; 424/130.1, 131.1, 134.1, 424/137.1, 138.1, 141.1, 143.1, 152.1, 155.1, 424/156.1, 183.1
See application file for complete search history.

(56) References Cited

U.S. PATENT DOCUMENTS

| | | | |
|---|---|---|---|
| 4,219,411 A | 8/1980 | Yen et al. | |
| 4,510,244 A | 4/1985 | Parks et al. | |
| 4,659,678 A | 4/1987 | Forrest et al. | |
| 4,710,472 A | 12/1987 | Saur et al. | |
| 4,752,569 A | 6/1988 | Terasaki et al. | |
| 4,857,452 A | 8/1989 | Ho | |
| 4,920,061 A | 4/1990 | Poynton et al. | |
| 5,019,497 A | 5/1991 | Olsson | |
| 5,095,097 A | 3/1992 | Hermentin et al. | |
| 5,185,254 A | * | 2/1993 | Linnenbach |
| 5,194,300 A | 3/1993 | Cheung | |
| 5,219,763 A | 6/1993 | Van Hoegaerden | |
| 5,256,532 A | 10/1993 | Melnicoff et al. | |
| 5,264,344 A | 11/1993 | Sneath | |
| 5,290,707 A | 3/1994 | Wood | |
| 5,322,678 A | 6/1994 | Morgan, Jr. et al. | |
| 5,326,696 A | 7/1994 | Chang | |
| 5,340,719 A | 8/1994 | Hajek et al. | |
| 5,374,531 A | 12/1994 | Jensen | |
| 5,405,784 A | 4/1995 | Van Hoegaerden | |
| 5,422,277 A | 6/1995 | Connelly et al. | |
| 5,424,213 A | 6/1995 | Mougin | |
| 5,491,068 A | 2/1996 | Benjamin et al. | |
| 5,514,340 A | 5/1996 | Lansdorp et al. | |
| 5,536,644 A | 7/1996 | Ullman et al. | |
| 5,624,815 A | 4/1997 | Grant et al. | |

FOREIGN PATENT DOCUMENTS

| | | |
|---|---|---|
| EP | 016 552 | 10/1980 |
| EP | 098 534 | 1/1984 |
| EP | 131 934 | 1/1985 |
| EP | 241 042 | 10/1987 |
| EP | 339 769 | 11/1989 |
| EP | 403960 | 6/1990 |
| EP | 395 355 | 10/1990 |
| EP | 537 827 | 4/1993 |
| WO | WO 90/07380 | 7/1990 |
| WO | WO 90/10692 | 9/1990 |
| WO | WO 91/01368 | 2/1991 |
| WO | WO 91/09938 | 7/1991 |
| WO | WO 91/15766 | 10/1991 |
| WO | WO 92/04961 | 4/1992 |
| WO | WO 94/07142 | 3/1994 |
| WO | WO A1 94/07139 | 3/1994 |
| WO | 95/24648 | 9/1995 |
| WO | WO 96/31777 | 10/1996 |

OTHER PUBLICATIONS

Gura (Science, 278:1041–1042), 1997.*
Parry et al (J. Cell Science, 101:191–199), 1997.*
William P. Peters, et al.: "High–Dose Chemotherapy and Autologous Bone Marrow Support as Consolidation After Standard–Dose Adjuvant Therapy for High–Risk Primary Breast Cancer", *Journal of Oncology*: Jun. 1993; vol. 11, No. 6, pp. 1132–1143.
James O. Armitage, M.D.; "Bone Marrow Transplantation"; *New England Journal of Medicine*; Mar. 24, 1994; vol. 330, No. 12, pp. 827–838.
Thomas J. Moss, et al.; "Contamination of Peripheral Blood Stem Cell Harvests by Circulating Neuroblastoma Cells"; *Blood*, 1990; vol. 76, No. 9, pp. 1879–1883.

(Continued)

Primary Examiner—Susan Ungar
(74) Attorney, Agent, or Firm—Merchant & Gould P.C.

(57) ABSTRACT

A method for killing unwanted target cells in a cell population comprising nucleated cells harvested from peripheral blood, or CD-34+ or similar early progenitor cells selected from the above nucleated cells or from bone marrow aspirates, in which method the cell population is in vitro or in vivo exposed to two or more immunotoxins selectively killing the malignant cells, is described. Furthermore the invention relates to the mixture of immunotixins, the use of the mixture and a kit for performing the method.

19 Claims, No Drawings

OTHER PUBLICATIONS

Amy A. Ross, et al.; "Detection and Viability of Tumor Cells in Peripheral Blood Stem Cell Collections From Breast Cancer Patients Using Immunocytochemical and clonogenic Assay Techniques"; *Blood*; 1993; vol. 82, No. 9, pp. 2605–2610.

Malcolm K. Brenner, et al.; "Gene–marking to trace origin of relapse after autologous bone–marrow transplantation"; *Lancet*; 1993, pp. 85–86.

John G. Grivven, M.D., et al.; "Immunologic Purging of Marrow Assessed by PCR Before Autologous Bone Marrow Transplantation for B–Cell Lymphoma"; *New England Journal of Medicine*; Nov. 28, 1991; vol. 325, No. 22, pp. 1525–1533.

Elizabeth J. Shpall, et al., "Release of Tumor Cells from Bone Marrow"; *Blood*; Feb. 1, 1994; pp. 623–625.

Wolfram Brugger, et al.; "Mobilization of Tumor Cells and Hematopoietic Progenitor Cells Into Peripheral Blood of Patients With Solid Tumors"; *Blood*; 1994; vol. 83, No. 3, pp. 636–640.

Ger J. Strous, et al.; "Mucin–Type Glycoproteins"; *Critical Reviews in Biochemistry and Molecular Biology*; 1992; pp. 57–92.

Lou de Leij, et al.; "The Use of Monoclonal Antibodies for the Pathological Diagnosis of Lung Cancer"; In: H.H. Hansen (ed), Lung Cancer: Basic and Clinical Aspects; Boston: Martinus Niijhoff Publishers, 1986; pp. 31–48.

Aslak Godal, et al.; "Immunotoxins directed Against the High–Molecular–Weight Melanoma–Associated Antigen. Identification of Potent Antibody–Toxin Combinations"; *Int. J. Cancer*; 1992; pp. 631–635.

V.D. Courtenay, et al; "An In Vitro Colony Assay For Human Tumours Grown in Immune–Suppressed Mice and Treated In Vivo with Cytotoxic Agents"; *Br. J. Cancer*; 1978; pp. 261–268.

M.Y. Wang, et al.; "An effective immunomagnetic method for bone marrow purging in T cell malignancies"; *Bone Marrow Transplantations*; 1992; pp. 319–323.

Arne T. Myklebust, et al.; "Comparison of Two Antibody–based Methods for Elimination of Breast Cancer Cells from Human Bone Marrow"; *Cancer Research*; 1994; pp. 209–214.

Connie J. Eaves; "Peripheral Blood Stem Cells Reach New Heights"; *Blood*; 1993; pp. 1957–1959.

Elizabeth J. Shpall, et al.; "Transplantation of Enriched CD34–Positive Autologous Marrow Into Breast Cancer Patients Following High–Dose Chemotherapy: Influence of CD34–Positive Peripheral–Blood Progenitors and Growth Factors on Engraftment"; *Journal of clinical Oncology*; 1994; vol. 12, No. 1, pp. 28–36.

Michael J. Bjorn, et al.; "Antibody–Pseudomonas Exotoxin A Conjugates to Human Breast Cancer Cells in Vitro"; *Cancer Research*; Jul. 1986; pp. 3262–3267.

1989 Ian c. Anderson, et al.; "Elimination of Malignant Clonogenic Breast Cancer Cells from Human Bone Marrow"; *Cancer Research*; pp. 4659–4664.

K.C. O–Briant, MS, et al.; Elimination of Clongenic Breast Cancer Cells from Human Bone Marrow ; *Cancer*; 1991; pp. 1272–1278.

C.L. Tyer, et al.; "Breast Cancer Cells are Effectively Purged from Peripheral Blood Progenitor cells Using an Immunomagnetic Technique"; Abstract to First meeting of International Society for Hematotherapy and Graft Engineering, Orlando, Fl, 1993.

Firoenzo Stirpe, et al.; "Ribosome–Inactivating Proteins from Plants: Present Status and future Prospects"; *Bio/Technology*, Apr. 1992; vol. 10, pp. 405–412.

Luigi Barbieri, et al.; "Ribosome–inactivating proteins from plants"; *Biochimica et Biophysica Acta*; 1993; pp. 237–282.

R.M. Lemoli, et al.; "Positive selection of hematopoietic CD34+ stem cells provides 'indirect purging' of CD34–lymphoid cells and the purging efficiency is increased by anti–CD2 and anti–CD30 immunotoxins"; *Bone Marrow Transplantation*; 1994; pp. 465–471.

I.J. Diel, et al.; "Detection of Tumor Cells in Bone Marrow of Patients with Primary Breast Cancer: A Prognostic Factor for Distant Metastasis"; *Journal of Clinical Oncology*; 1992; pp. 1534–1539.

Arne T. Muklebust , et al.; "Eradication of Small Cell Lung Cancer Cells from Human Bone Marrow with Immunotoxins"; *Cancer Research*; 1993; pp. 3784–3788.

K.M. Stray, et al.; "Purging Tumor Cells from Bone Marrow or Peripheral Blood Using Avidin–Biotin Immunoadsorption"; *Advances in Bone Marrow Purging and Processing*; 1994; Orlando:Wiley–Liss, Inc.; pp. 97–103.

D. Pilling, et al.; "The kinetics of interaction between lymphocytes and magnetic polymer particles"; *National Library of Medicine*, File Medline, Medline accession No. 90010165; Sep. 1, 1989; 122(2) pp. 235–241.

R.M. Leven, et al.,; "Immunomagnetic bead isolation of megakaryocytes from guinea–pig bone marrow: effect of recombinant interleukin–6 on size, ploidy and cytoplasmic fragmentation"; *National Library of Medicine*, File Medline, Medline accession No. 07671620; Br J Haematol Mar. 1991; 77 (3), pp. 267–273.

Jan. 1993, Bio/Technology, vol. 11, Bjorn–Ivar Haukanes et al., "Application of Magnetic Beads in Bioassays" p. 60.

1990, Scand J. Immunol, vol. 31, J. Heldrup, "A New Technique Using an Aggregating Antibody Against Glycophorin in–A for Puring Ficoll–Paque–Separated Leucocytes of Contaminating Erythroid Lineage Cells", p. 289–p. 296, see "Materials and methods" and p. 295, right column.

Rye, et al.; "Immunobead Filtration";*American Journal of PAthology*; Jan. 1997; vol. 150, No. 1, pp. 99–107.

A. Bennick et al.; "A Rapid Method for Selecting Specific Hybridoma Clones using Paramagnetic Dynabeads"; *Scand. J. Immunol.*; 1993; pp. 212–214.

Hitoshi Maeda; "Applicability of an Immuno–microsphere Technique for a Forensic Identification of ABO Blood Types: The Use of Fluorescent Microspheres"; *Jpn J. Legal Med.*; 1989; pp. 322–327.

Andrew J. Beavis, et al.; "Detection of Cell–Surface Antigens Using Antibody–Conjugated Fluorosphers (ACF): Application for Six–Color Immunofluorescence"; *Biotechniques*; 1996; pp. 498–503.

Derwent acession No. 93–173192, Toyobo KK: "Sensitivity detection of ligand–receptor reaction–by combining fluorescent fine particles with objective substance, passing mixt. through flow cytometer, counting number of agglomerates etc."; & JP,A,5107249, 9304427, DW9321.

K.A. Muirhead, et al.; "Flow Cytometry: Present and Future"; *Biotechnology*; Apr. 1985; vol. 3, pp. 337–356.

W. Kemmner, et al.; "Separation of tumor cells from a suspension of dissociated human colorectal carcinoma tissue by means of monoclonal antibody–coated magnetic beads"; *Journal of Immunological Methods*; 1992; pp. 197–200.

C.I. Civin, et al.,; "positive stem cell selection—basic science"; *Progress in Clinical and Biological Research*; vol. 333, 1990, pp. 387–402.

E.H. Dunlop, et al.; "Magnetic separation in biotechnology"; *Biotech ADVS*; vol. 2, 1984, pp. 66–69.

C.H. Setchell; "Magnetic Separations in Biotechnology-a Review"; *J. Chem. Tech. Biotechnol.*; vol. 35B, No. 3, 1985, pp. 175–182.

J.H. Pizzonia, et al.; "Immunomagnetic separation, primary culture, and characterization of cortical thick ascending limb plus distal convoluted tubule cells from mouse kidney"; *National Library of Medicine*, File Medline, Medline accession No. 07671620; Br J Haematol Mar. 1991; 77 (3), pp. 267–273.

G. Kvalheim, et al.; "Elimination of B–Lymphoma Cells from Human Bone Marrow: Model Experiments Using Monodisperse Magnetic Particles Coated with Primary Monoclonal Antibodies"; *Cancer Research*; vol. 47, Feb. 1987, pp. 846–851.

J.T. Kemshead, et al.; "Monoclonal antibodies and magnetic microspheres for the depletion of leukamic cells from bone marrow harvested for autologous transplantation"; *Bone Marrow Transplantation*; 1987; vol. 2, pp. 133–139.

G. Kvalheim, et al., "Immunomagnetic purging of B–lymphoma cells from human bone marrow", *Dialog Information service*, File 159, Cancerlit, Dialog accession No. 00559663; Fourth European Conference on Clinical Oncology and Cancer Nursing, Nov. 1–4, 1987, Madrid, Federation of European Cancer Societies, pp. 262, 1987.

T. Lea, et al.; "Monosized, magnetic polymer particles: their use in separation of cells and subcellular components, and in the study of lymphocyte function in vitro"; *National Library of Medicine*, File Medline, Medline accession No. 90234499; J. Mol. Recognit.; Feb. 1988; 1(1), pp. 9–18.

"Making the most of mucin: a novel target for tumor immunotherapy", Barratt–Boyes SM, Cancer Immunol Immunother. Nov. 1996; 43(3): 142–51.

The Epithelial Glycoprotein 2 (EGP–2) Promoter–driven Epithelial–specific Expression of EGP–2 in Transgenic Mice: A New Model to Study Carcinoma–directed Immunotherapy:, McLaughlin et al., Cancer Research 61, 4105–4111, May 15, 2001.

"Selection and Characterization of Anti–MUC–1 scFvs Intended for Targeted Therapy", Winthrop et al., Clinical Cancer Research, vol. 9, 3845s–3853s, Sep. 1, 2003 (Suppl.).

"Kinetics of Uptake and Degradation of an Abrin Immunotoxin by Melanoma Cells and Studies of the Rates of Cellular Intoxication", Godal et al., Int. J. Cancer: 42, 400–404 (1988).

"Studies on the Mechanism of Action of Abrin–9.2.27 Immunotoxin in Human Melanoma Cell Lines", Godal et al., Cancer Research 47, 6243–6247, Dec. 1, 1987.

"Systematic Immunotoxin Treatment Inhibits Formation of Human Breast Cancer Metastasis and Tumor Growth in Nude Rats", Engebraaten et al., Int. J. Cancer: 88, 970–976 (2000).

"A Murine cDNA Encodes a Pan–Epithelial Glycoprotein that is also Expressed on Plasma Cells", Bergsagel et al., The Journal of Immunology, vol. 148, 590–596, No. 2, Jan. 15, 1992.

"Molecular cloning of cDNA for the carcinoma–associated antigen GA 733–2", Szala et al., Proc. Natl. Acad. Sci. USA, vol. 87, pp. 3542–3546, May 1990 Biochemistry.

"Molecular Cloning and Characterization of a Human Adenocarcinoma/Epithelial Cell Surface Antigen Complementary DNA", Strnad et al., Cancer Research 49, 314–317, Jan. 15, 1989.

Appendix 3–6, "Monoklonaler Antikorper BM7" and Appendix 3–7, "Monoklonaler Antikorper BM2", Brummend et al., Cancer Research, 1994, 54: 4162–4168.

"Pharmacokinetics and Scintigraphy of Indium–111–DTPA–MOC–31 in Small–Cell Lung Carcinoma", Kosterink et al., The Journal of Nuclear Medicine–vol. 36, No. 12, Dec. 1995.

"Can therapeutic concentrations of the anti EGP2 immunotoxin conjugate MOC31–PE be achieved in patients with antigen positive carcinomas? A phase I study in patients with advanced mammary, lung, colorectal or prostate carcinoma", Aamdal et al., pp. 1–24.

Abstact of Acession No. 90658782 Cancerlic, "Fourth International Conference on Monocional Antibody Immunoconjugates for Cancer", Mar. 30 to Apr. 1, 1989, San Diego, CA, UCSD Cancer Center.

Dialog Information Service, File 159, Cancerlit, Dialog accession No. 01046200, Cancerlit accession No. 94290389, Lemoli RM et al; "Positive selection of hematopietic CD34+ Stem cells provides 'indirect purging' of CD34–hymphoid cells and the purging efficiency is increased by anti–CD2 and anti–CD30 immunotoxins", Bone Marrow Transplant: 13(4):465–71, 1994.

Dialog Information Service, File 159, Cancerlit, Dialog accession No. 01018250, Cancerlit accession No. 94084695, Myklebust AT et al: "Comparison of two antibody–based methods for elimination of breast cancer cells from human bone marrow", Cancer Res; 54(1):209–14, 1994.

Dialog Information Service, File 159, Cancerlit, Dialog accession No. 00447849, Cancerlit accession No. 86110672, Tonevitsky AG et al: "Elimination of Marine Erythroleulemic Stem Cells with a Novel Anti–Eryhroid Antibody Conjugated to Ricin a–chain: A Model for Studies of Bone–Marrow Transplantation Therapy", Int. J. Cancer, 37(2):263–73, 1986.

Dialog Information Service, File 159, Cancerlit, Dialog accession No. 01268628, Cancerlit accession No. 97091812, Kvalheim G. et al: "Purging of tumor cellsfrom leulespheresis products: experimental and clinical aspects", J. Hematother: 5(4):427–36, 1996.

Abstract of Crews J.R. et al.; *Int. Journ. of Cancer*; Jul. 9, 1992; vol. 51, No. 2.

* cited by examiner

METHOD OF KILLING TARGET CELLS IN HARVESTED CELL POPULATIONS WITH ONE OR MORE IMMUNO-TOXINS

The present invention relates to selective purging of a cell population for target cells by exposing the cell population to a combination of two immunotoxins.

So called autologous stem cell transplants comprise isolated cells from blood or bone marrow from cancer patients which after pretreating the patients contain adequate amounts of immature progenitor blood and immune cells to restore the function of a non-functioning bone marrow shortly, or over a longer period of time after reinstalling the cells in the blood of the patients from which the cells are harvested.

Purging of autologous haematopoietic transplants using antibodies is known in the art when the transplants represent unselected bone marrow samples. Such a purging is published i.a. by Myklebust, A. T., Godal, A., Juell, S. and Fodstad, Ø. "Comparison of two antibody-based methods for elimination of breast cancer cells from human bone marrow". Cancer Res. (USA) 1994, 54/1 (209–214) and Myklebust, A. T., Godal, A., Pharo, A., Juell, S. and Fodstad, Ø. "Eradication of small cell lung cancer cells from human bone marrow with immunotoxins", Cancer Res. (USA) 1993, 53(16), 3784–88. Both publications use immunotoxins in which the antibody is conjugated to a toxin. The principle is to kill malignant cells from the harvested bone marrow cells before reinjection of the cell suspension into the patient.

In the recent years it is developed methods in which the principle actually is the opposite. Using the so called stem cell transplantation one tries to positively select from blood or bone marrow a subgroup of normal cells which are able to restore normal bone marrow function after the cells are reinstalled in the patient. These "stem cells" consist of a mixture of the most immature precursors for blood and immune cells and also more differentiated cells. The harvest of such cells can be performed either by so called apharesis of peripheral blood, a procedure taking one or more days, or by immuno-absorption/selection of $CD34^+$ cells (immature progenitor cells) from blood or bone marrow using different techniques known in the art.

Stray, K. M. et al., "Purging tumor cells from bone marrow or peripheral blood using avidin, biotin, immuno adsorption" In: P. G. Adrian, G. Samuel and A. W—W. Diana (Eds), Advances in bone marrow purging and processing, pp. 97–103, Orlando: Willelis Inc., 1994 describes purging of bone marrow cells or an apharesis product from peripheral blood. This procedure is performed for purging in patients with lymphoma and in patients with breast cancer. The method includes an enrichment step for $CD34^+$ cells before purification of B-cells or breast cancer cells with a so-called avidin column. In this case the purging is performed indirectly in that the cell suspension initially is incubated with primary antibodies which bind to the breast cancer cells, the cell suspension is washed and once more incubated with an antibody which bind to the primary antibodies. This rat antibody is biotinylated, i.e. connected to a molecule which binds strongly to avidin. When this cell suspension finally is loaded on a column with avidin conjugated beads the tumor cells are trapped by the binding between cells with primary antibody-biotinylated secondary antibody-avidin. The results of purging using such a system was at the most 3.2 log depletion of malignant cells. The principle is very time-consuming and cumbersome since the cell suspension must be handled in several steps including incubation with antibody and two washes before it is loaded on to the column. Thus, it is difficult to avoid damage to the stem cells or that there is unspecific trapping of the stem cells in the column, resulting in unfortunate loss of cells crucial for the recovery of normal bone marrow function.

Tyer, C. L. et al., "Breast cancer cells are effectively purged from peripheral blood progenitor cells using an immunomagnetic technique". Abstract to the first meeting of International Society for Hematotherapy and Graft Engineering, Orlando Fla., 1993 describes an immunomagnetic method similar to the one used in the publication of Myklebust et al. above. This method is, however, used on peripheral blood cells. This principle is also entirely different from the use of immunotoxins and the effectivity of the purging varied from 3.3 to 4.8 log depletion of malignant cells in model experiments. The abstract does not mention any additional use of an indirect system with incubation of primary antibodies followed by washing and new incubation with beads connected to antibodies which bind to the primary antibody, but this is a reasonable assumption. Also this procedure comprises additional and possibly traumatic treatment of the normal cells and the procedure is time requiring. The effectivity is limited and the abstract does not mention anything about purging of $CD34^+$ cell populations which will be a major problem with this method, as selection of $CD34^+$ cells per se is time requiring and laborious. Thus, in most cases an immunomagnetic principle is used for $CD34^+$ cell selection, which in this example is followed by one or two immunomagnetic steps for purging purposes. Therefore, there is a considerable risk for cell destruction and cell loss, with a method requiring a long lasting procedure and involving high costs.

Lemoli, R. M. et al. (1994) Bone Marrow Transplant 13: 465–471 describe purification of human $CD34^+$ hematopoietic cells using the avidin-biotin immunoabsorption technique. They increased the purging of neoplastic cells by using several immunotoxins containing the ribosome-inactivating protein saporin and directed toward the lymphoid associated antigens CD30 and CD2. Tecce, R. et al (1991) Int. J. Cancer, 49: 310–316 describe purging autologous bone marrow prior to transplantation in patients suffering from monocytic leukemia with 2 monocytic-cell-lineage-specific immunotoxins constructed with saporin and 2 MoAbs of high specificity for circulating monocytes and M5b acute nonlymphoid leukemia (ANLL). In WO91/09058 it is described immunotoxins comprising the myelomonocytic specific MoAb 195 useful for purging ANLL from bone marrow. Tonevitsky, A. G. et al (1986) Int. J. Cancer, 37: 263–273, describe purging of murine erythroleucemic stem cells from bone marrow employing an immunotoxin comprising a conjugate of ricin-A-chain and MoAb MAE15 which binds to the surface of normal and neoplastic murine erythroid cells: a model for studies of bone marrow transplantation therapy.

In isolating stem cells for transplantation one of the main objectives was that the cells which is intended to be reinstalled in the patients are selectively isolated in such a way that the transplants should not contain any malignant cells. In prior art it was recently shown that such preparations of stem cells surprisingly comprises malignant cells in a significant number of the examined cases. Up to now, very limited efforts have been made to remove or kill selected malignant cells in such transplants. This is partly because the skilled person of the art has not seen the need, and also because it was expected that the actual known methods were not specific and thus also would kill or remove the vulnerable stem cells. Furthermore, a supply of bone marrow or mobilized peripheral blood from a patient is not simple and unlimited and such a method for purging of stem cell transplants has to be performed within a short period of time and must be uncomplicated in order to avoid loss of, or damage to the normal cells can. Thus, referring to the above, the reason for using stem cell transplants is partly that the transplant should be completely free of cancer cells, partly that reconstitution of bone marrow function is faster than after transplantation with unselected bone marrow. It follows that it was absolutely necessary to invent a method which leave the fragile normal stem cells intact and which is practical to perform in combination with stem cell isolation procedures.

The object of the present invention is therefore to provide a method for purging of stem cell transplants which do not comprise the above disadvantages.

Such objects are obtained by the present invention characterized by the enclosed claims.

The present invention relates to purging of harvested stem cell populations in cases of solid tumors in which method the cell population is exposed to a composition of two or more antibodies connected to bacterial toxins. The used antibodies are directed to target cell-associated antigens.

In one aspect, the invention provides a method to kill breast cancer or other carcinoma cells expressing the same antigens in a cell population comprising nucleated cells harvested from peripheral blood, or CD-34× cells selected from the above nucleated cells, or other immature/early progenitor cells from blood containing multipotent stem cells, wherein the cell population is exposed to a combination of two immunotoxins, wherein each immunotoxin is composed of a conjugate between an antibody and a cell toxin, fragments of antibodies and toxin, or recombinantly produced antibodies, toxins, immunotoxins or fragments thereof, wherein the antibodies are directed to epitopes on the antigen EGP2 expressed by the gene GA733 and to epitopes on the antigen expressed by the genes MUG 1, MUC2 or MUG 3, respectively or a combination of these, and the toxin is Pseuctomonas exotoxin A.

In the following the invention is described in more detail by using an example of purging of stem cell transplants harvested from peripheral blood to remove breast cancer cells.

Known techniques to harvest cells comprise immunoadsorption/selection of peripheral blood stem cells (PBSC) or CD-34$^+$ cells from blood or bone marrow. However, there are no known harmless and sufficiently effective techniques for purging of these cell populations for tumor cells. It seems evident that even among these immature cells there are malignant cells which according to prior knowledge should not posess CD34 receptors. Importantly, the invention described below surprisingly purged also the cancer cells without toxicity to normal progenitors.

Before harvesting a stem cell transplant from peripheral blood it is necessary to mobilize the stem cells from the bone marrow by using chemotherapy or treatment with growth factors by methods known in the art. The harvesting of stem cells can be performed according to one or several methods, dependent on what kind of cells is desired. In one method peripheral blood stem cells are collected. This can be performed by scheduling patients to undergo leukapheresis on days 10 and 11 of G-CSF administration (10 µg/kg/day) after receiving high doses of chemotherapy and total body irradiation. Blood flow rate may be fixed at for example 70 ml/min by using a CS-300 Plus blood cell separator (Baxter Healthcare Corporation, Fenwal Division, Deerfield, Ill., USA). The average volume of blood treated during such a procedure may be about 10 liters for 2½ hour to a dual-lumen central venous catheter. Fifty ml of PBSC may be collected and washed with phosphate buffer saline (PBS), 1% human serum albumin (HSA) in a Cobe Processor 2991 to remove platelets. For use in the present invention the concentration of cells (2–4×10$^{10}$/apharesis) can be regulated to 1×10$^8$/ml for negative selection (purging) with immunotoxins.

If CD-34$^+$ cells are desired this may be obtained by a positive selection with ISOLEX 50® or ISOLEX 300® (Baxter). In this method the product from apharesis or from bone marrow, which may be about 4×10$^{10}$ to 6×10$^{10}$ cells, can be mixed together and incubated with e.g. anti-CD34$^+$-monoclonal antibody 9C5 at 0.5 µg/1×10$^6$ cells at 4° C. for 30 minutes on a gentle rotator. The treated cells are washed with PBS with 1% HSA on Cobe Processor to remove unbound antibody. DYNAL® beads M-450 are added to the CD34$^+$ fraction at 0,5 beads per 1 nucleated cell at 4° C. for 30 minutes. Magnetic separation of rosettes from non-targeted cells can be performed by washing away unbound cells two or three times with PBS, 1% HSA. The CD34$^+$ cells can then be released from the Dynal® beads by adding, for example ChymoCell-R (Chymopapain) at a final concentration of 200 pKat/ml in 15 minutes at room temperature. Thus CD34$^+$ cells can be harvested by washing with PBS in 5% sodium citrate. Also other procedures for selecting stem cells/early progenitor cells are known.

The binding profile of several antibodies in breast cancer cell lines and tumor materials has been examined by others and partly confirmed by us. The antibodies which bind to a large percent of breast cancer cells and not to important immature normal cells in blood and bone marrow, were conjugated to Pseudomonas exotoxin A (PE) and the ability to kill breast cancer cells in culture was examined, mainly in colony producing assays. Based on the binding profile of the antibodies the present inventors produced in all five different immunotoxins:

1. MOC31-PE: This conjugate binds to a very high percent of all breast cancer cells and was very effective in the model experiments and in the actual concentrations with marginal toxicty to normal hematopoietic progenitor cells.
2. NrLu10-PE: This binds to the same antigen as above, but to another epitope. It is slightly less active than MOC31-PE.
3. BM7-PE: This binds to the protein part of a mucin antigen which mainly is found on breast cancer cells. The antigen is present on a great percentage of breast cancer cells, but not all. The immunotoxin showed high specific activity to the cancer cells, but was not as effective as the two previous immunotoxins.
4. BM2-PE: This binds to a sugar containing epitope on the same antigen as BM7-PE. The immunotoxin showed approximately the same effectivity as BM7-PE concomitant with a very low toxicity for normal cells.
5. MLuC1-PE: This binds to a totally different antigen, the Lewis$^Y$-antigen. The immunotoxin was slightly less active than the previous one and also showed a moderate toxicity to normal cells.

The immunotoxins according to 1, 2, 5 were tried individually and in combination in model experiments of purging regular bone marrow samples for cancer cells (Myklebust et al., Cancer Research, 1994). It is, as already mentioned, a great advantage to use stem cell transplants because of a shorter interval to regain normal bone marrow function (i.e. safer procedure). However, in spite of what was expected, such transplants are contaminated with tumor cells and it was necessary to apply immunotoxins able to kill all cancer cells in the transplant without significantly affecting the normal cells.

Search for immunotoxins more specific for breast cancer than MLuC1-PE and better suited for purging in breast cancer was initiated.

During this search it was surprisingly discovered that the combination of MOC31-PE and BM7-PE were more effective than the sum of each of the previous immunotoxins used alone. This is demonstrated in Table 1 below. Further studies of binding between the antibody and the cell lines have shown that the combination result in a stronger binding than the single antibodies.

MOC31 binds to most of the breast cancer cells, also those which are less differentiated. BM7 recognizes a mucin antigen which is expressed on a considerable fraction of breast cancer cells, also on the cells which are more differentiated. NrLu10 and BM2 bind to the antigen recognized by MOC31 and BM7, respectively, and with this in mind it was not very probable that they would add anything to a combination of MOC31 and BM7 immunotoxins. MLuC1-PE was theoretically interesting in that it is binding to a different antigen than the immunotoxins mentioned above. MLuC1-PE was however, toxic for normal cells and the model experiments did not show any clear advantage by including this in the combination.

In the example below, purging of peripheral stem cell transplants (apharesis products) is described. In addition, the inventors have performed several experiments using the combination MOC31-PE and BM7-PE in experiments where tumor cells are added to harvested peripheral stem cells or bone marrow before an immunomagnetic positive selection of CD-34$^+$ cells. The results from one such experiment is shown in Table 2. With two different cell lines it is demonstrated that the positive selection of CD34$^+$ cells in itself (without any other form of purging) removes up to 3.8 log tumor cells from the original harvested cell population. In other experiments the "purging" effect of CD34 selection varies from 2–3 log which also is referred to in the literature. When the immunotoxin treatment was used on the positively selected CD34 population the total purging effect was more than 4.7 log (Table 2) for both cell lines. More than 4.7 log means in this case that all detectable tumor cells were removed. In other experiments we have in separate assays grown tumor cells and normal progenitor cells taken from CD34$^+$ population after 1 hour treatment with immunotoxin. In these experiments we observed that the tumor cells are killed or dying shortly after treatment while the tumor cells in unpurged control populations grew and created colonies, and/or proliferated in cell-adherence type cultures. The normal stem cells are not influenced by the treatment such that in three different test systems the survival of the normal progenitor cells are only insignificantly reduced. Table 3 shows a similar experiment in which the CD34$^+$ cells were incubated with the immunotoxins for 2 hours at 37° C. and it is demonstrated that the stem cells essentially survive the immunotoxin treatment.

TABLE 1

Effect of immunotoxins involving PE in killing PM1 breast cancer cells

| PE-Immuno-toxin with MAbs | Exp | Log cell kill at Immunotoxin concentration of | | |
|---|---|---|---|---|
| | | 0.01 µg/ml mean ± s | 0,1 µg/ml mean ± s | 1,0 µg/ml mean ± s |
| BM2 | 3 | 0.01 ± 0.01 | 0.27 ± 0.09 | 2.38 ± 0.38 |
| BM7 | 3 | 0.13 ± 0.11 | 0.64 ± 0.15 | 2.55 ± 0.40 |
| MLuC1 | 3 | 0.10 ± 0.13 | 0.36 ± 0.19 | 2.10 ± 0.68 |
| MOC31 | 3 | 0.81 ± 0.10 | 2.83 ± 0.29 | >5 |
| BM2 + MOC31 | 4 | 1.20 ± 0.26 | >5 | >5 |
| BM7 + MOC31 | 4 | 1.16 ± 0.26 | >5 | >5 |
| MLUC1 + MOC31 | 4 | 1.14 ± 0.36 | >5 | >5 |
| BM2 + BM7 MLuc1 + MOC31 | 2 | 1.15 ± 0.2–1.55 ± 0.6 | >5 | >5 |

TABLE 2

Purging effects of positive immunomagnetic selection of CD34$^+$ alone and combined with anti-breast carcinoma MOC31 and BM7 immunotoxin, in model experiments with PM1 and T-47D breast cancer cells admixed (1%) to peripheral blood stem cells.

| | PM1 | | | T-47D | | |
|---|---|---|---|---|---|---|
| Method | No. of experiments performed | No. of cells depleted | Log cell killed | No. of experiments added | No. of cells depleted | Log cell killed |
| Positive selection of CD34$^+$ cells | 2 | 5 × 10$^4$ | 3.8 ± 0.04 | 2 | 5 × 10$^4$ | 3.7 ± 0.04 |
| Positive selection of CD34$^+$ cells followed by IT treatment | 2 | 5 × 10$^4$ | >4.7 | 2 | 5 × 10$^4$ | >4.7 |

$^a$Calculated from observed number of colonies, taking into account the plating efficiency, of the number of cell killed by the treatment.
$^b$Mean of the results obtained in indpendent experiments, each performed in triplicate.
$^c$MOC31-PE and BM7-PE immunotoxin were used at a concentration of 1 µg/ml of each.

TABLE 3

Effect of IT on the survival of colonies in CD34+ cells selected from mobilized peripheral blood. One ×10$^5$ CD34+ cells were incubated with the immunotoxins for 2 h at 37° C., seeded out in CFU-GM and CFU-GEMM (5 × 10$^3$/dish) cultures, and assayed as described in "Material and Methods" in the Example.

| Treatment | Concentration of each IT (ug/ml)$^a$ | CFU-GEMM No. of colonies mean ± SD$^b$ | %$^c$ | BFU-E No. of colonies mean ± SD$^b$ | %$^c$ | CFU-GM No. of colonies mean ± SD$^b$ | %$^c$ |
|---|---|---|---|---|---|---|---|
| None | 1.0 | 456 ± 118 | (100) | 193 ± 31 | (100) | 85 ± 6 | (100) |
| MOC31-PE + | 2.5 | 432 ± 56 | (95) | 172 ± 31 | (89) | 65 ± 6 | (77) |
| BM7-PE | | 412 ± 118 | (90) | 166 ± 14 | (86) | 45 ± 8 | (53) |

It was very surprising that the use of two antibodies, directed to antigens expressed by epithelial cells according to the present invention, each combined with the Pseudomonas exotoxin A bacterial toxin, killed the malignant cells without performing any damage to the normal stem cells in the harvests from peripheral blood and bone marrow. It is known in the art that cells can be killed by bacterial exotoxins and that the killer effect is increased by connecting the toxin to antibodies directed to epitopes expressed by the target cells. However, it is also known that if immature cells are exposed to one or several immunotoxins it is a profound possibility that this treatment kills the normal stem cells in the cell population. Furthermore, these normal stem cells are sensitive to ex vivo treatment accompanying mechanical traumas and temperature changes. In the present invention the cell population, for example a stem cell transplant harvested from peripheral blood, is exposed to a composition of two antibodies each conjugated to PE. Since one of the immunotoxins was exceedingly active it is surprisingly demonstrated that by using a composition of two antibodies connected to a bacterial toxin the purging effect seemed greater than the sum of the effects when the immunotoxins are used separately. This synergistic effect is demonstrated in table 4 of the present disclosure using the antibodies BM7 and MOC31 connected to Pseudomonas exotoxin A in killing PM1 human breast cancer cells. The immunotoxins are both monoclonal antibodies directed against tumor associated antigens connected to the bacterial toxin Pseudomonas exotoxin A. One of the antibodies recognizes a epithelial antigen coded for by the GA733-2 gene, which is expressed by most of the carcinoma cells and therefore can be used in all cases involving carcinomas (for example breast cancer, colorectal cancer, prostate cancer, ovarial cancer, lung cancer and pancreatic cancer). The other antibody is directed to mucin, a mucus protein which is slightly different from one carcinoma type to another. Commonly the antigen can be described as proteins encoded by the genes MUC-1, MUC-2 and MUC-3. Examples of the above mentioned monoclonal antibodies are MOC31 and BM7.

Conjugation of antibody and toxin can be performed in different known ways. Selection of two or more antibodies in the composition for linking to the bacterial exotoxins was performed in such a way that antibody binding was directed to epitopes expressed on a majority of the target cells and not on the normal cells. The problem in prior art is that both malignant cells and normal blood cells express common antigens on the cell surface. In the example enclosed in the present disclosure the two monoclonal antibodies MOC31 and BM7 are used. The former of these antibodies are directed to epithelial cells which if found in peripheral blood, are malignant. The antigen (the whole protein) is encoded by the gene GA 733-2. This antigen has, however, several epitopes and it is important to target the epitopes most abundantly expressed.

The BM7 antibody is one of the antibodies directed to an epitope of the antigen expressed by the MUC1 gene. Several genes encode similar antigens e.g. (MUC2, MUC3).

The bacterial toxin Pseudomonas exotoxin A has a relatively moderate toxic effect on normal stem cells and malignant cells. However, when connected to antibodies directed to antigens expressed on the target cells the toxic effect on these is very pronounced. In Table 5 it is demonstrated that the mixture of immunotoxins according to the invention, even after an incubation time of as little as 60 minutes, kills T-47 D cells, MCF7 cells and PM1 cells at a much higher degree of efficacy than known in the prior art with other methods. The combination of these two immunotoxins is thus giving surprising results in relation to what should be anticipated because of the selective efficacy, simplicity and the only marginal toxicity to normal progenitor cells.

It may be claimed that it is known to use several immunotoxins consisting of Pseudomonas exotoxin A conjugated to three different antibodies, see Myklebust et al. 1993 and 1994. One of the antibodies (MOC31) were used in a similar way to the present invention in order to purge unselected bone marrow cells. However, the other antibodies used do not seem to be optimal, among other things because one of them is directed to the same antigen as MOC31 and because the other (MLuC1) crossreact with normal cells and thereby the immunotoxin linked to this antibody could easily be toxic for the most immature stem cells. In the present invention on purging stem cell preparations we have prepared another monoclonal antibody which add to the effect of MOC31 and observe that the combination of these two antibodies used as immunotoxins give profoundly surprising results.

Due to the high specific activity of the disclosed immunotoxins it seems possible to administer the mixture for in vivo treatment of patients suffering from different types of carcinoma. If the cancer disease is limited it will be possible to inject or infuse each of them or the mixture intravenously for example when spreading of the disease to the bone marrow is demonstrated. It is further possible to inject the immunotoxins alone or in combination in patients with further spread of the disease with abdominal fluid (ascites) or with pleural effusion. A third possibility is to treat patients with spread of the cancer to the central nervous system. In this case the immunotoxins can be injected directly into the tumor tissue, into the spinal fluid or in the artery supplying blood to the brain.

It is not known to use these immunotoxins in vivo except that MOC31-PE has been used in a leptomeningeal tumor model for small cell lung cancer. BM7-PE is not described in the literature at all.

An important problem in using immunotoxins in vivo is that their half lives often are very short, i.e. the immunotoxins are broken down and removed from the blood before the concentration is adequately high in the tumor. In U.S. Pat. No. 5,322,678, Morgan et al. has patented a modification of the antibody part of a immunotoxin in order to reduce the problem with short half life in vivo. The present inventor suggests similar modification of the toxin part, a procedure not previously performed or known.

EXAMPLE 1

Effective purging of breast cancer cells from peripheral blood stem cell harvests with immunotoxins.

Introduction

High dose chemoradiotherapy with autologous hematopoietic stem cell support is being used with increasing frequency to treat patients with a variety of malignancies (1, 2). In the cases where this approach is unsuccessful, the most common reason is relapse of the disease, rather than toxicity, infections, and lack of engraftment (3). Importantly, there is a solid evidence that in patients receiving high dose treatment, reinfusion of autografts containing clonogenic tumor cells can contribute to relapse and influence outcome (4). Gene-marking studies of autografted cells have indicated that tumor cells remaining in reinfused bone marrow (BM) contributes to recurrence of the disease (5). This conclusion is further supported by results in patients with follicular lymphomas which indicate that efficient BM purging improves disease-free survival (6.)

Using sensitive immunocytochemical techniques tumor cell contamination can be observed in histologically normal bone marrow autografts in the range of 37–62% of breast cancer patients undergoing high dose treatment (7). Peripheral blood stem cell (PBSC) autografts collected by apharesis after pretreatment with hematopoietic growth factors and chemotherapy are used to an increasing extent in the belief that these products will have a low probability of containing tumor cells. However, recently it has been found that although tumor cell involvement is less extensive in PBSC autografts compared to BM harvests, malignant cells are still frequently found in mobilized PBSC collections from breast cancer patients (4, 7). In addition, recent findings show that chemotherapy and/or growth factors may mobilize tumor cells into the peripheral blood in patients both with and without prior detectable cancer cells in bone marrow (7, 8), results that further increase the risk of tumor cell contamination in PBSC grafts.

To avoid reinfusion of malignant cells, in vitro purging of PBSC autografts of breast carcinoma cells may be needed. Here we report a practical and rapid purging method, demonstrating that a 60 min incubation procedure with ITs directly added to the apheresis product selectively kills more than 5 log of tumor cells.

Material and Methods

Cell Line. The PM1 breast cancer cell line was established in our laboratory from ascitic fluid drawn from a patient with advanced disease. The MCF7 and T-47D cell lines were obtained from the American Type Culture Collection (Rockwille, Md.) (ATCC HTB 22 and ATCC HTB 133 respectively). Cells were cultured at 37° C. in a 5% $CO_2$ atmosphere in RPMI 1640 medium (RPMI) supplemented with 10% heat inactivated fetal calf serum (FCS) and antibiotics (100 U/ml of penicillin, 100 µg/ml of streptomycin). Medium and supplements were purchased from GIBCO (Paisley, UK).

Human Bone Marrow and Peripheral Blood Progenitor Cells. BM cells were obtained from healthy volunteer donors. The BM mononuclear cell (MNC) fraction was obtained by Lymphoprep® (Nycomed Pharma, Oslo, Norway) and washed twice in phosphate buffered saline (PBS) before being used in the experiments. PBSCs were prepared from non-Hodgkin lymphoma patients. To mobilize PBSCs the patients were pretreated with chemotherapy plus hematopoietic growth factors (G-CSF, Neupogen, Amgen/Hoffman-La Roche, Basel, Switzerland). Eleven to twelve days after chemotherapy, when the number of $CD34^+$ cells in the pheriphral blood is high, the stem cells were collected by the use of a CS-3000 Plus blood cell separator (Baxter Healthcare Corp., Fenwal Division, Deerfield, IL.).

Toxin, Antibodies, and Construction of Immunotoxins. The anti-MUC1 (9) antibody BM7 (IgG1) was a gift from S. Kaul (Frauenklinik, University of Heidelberg, Germany), and the anti-EGP2 (10) antibody MOC-31 (IgG2a) was kindly provided by L. de Leij (University of Groningen, The Netherlands), and by MCA Development (Groningen). PE was obtained from Swiss Serum and Vaccine Institute (Bern, Switzerland). Each antibody was conjugated to PE via a thioether bond formed with sulfo-succinimidyl-4-(N-maleimidomethyl)cyclohexane-1-carboxylate (Pierce, Rockford, Ill.) as described previously (11).

Immunotoxin Treatment. The effect of IT treatment on clonogenic breast cancer cell survival was tested by incubating $2\times10^6$ exponentially growing tumor cells in RPMI with FCS with the indicated concentrations of ITs at 37° C. with gentle agitation (100 rpm on an orbital incubator (Gallenkamp, Leicestershire, UK)) for varying periods of time, as indicated for each experiment. The cells were washed twice in PBS with 1% FCS before being seeded out in the clonogenic assay.

Mouse hybridoma expressing antibody BM7 was deposited under the Budapest Treaty on Nov. 5, 2003 with ATCC® and assigned Deposit No. PTA 5632. Mouse hybridoma expressing antibody BM2 was deposited under the Budapest Treaty Feb. 14, 2005 with ATCC® and assigned Deposit No. PTA-6582. The address for ATCC® is: American Type Culture Collection, P.O. Box 1549, Manassas, Va 20108.

In some experiments, 10% tumor cells were admixed to BM mononuclear cells or PBSCs, incubated with ITs washed and the effect assessed for tumor cell or hematopietic progenitor clonogenic cell survival.

Colony Assays for Tumor and Hematopoietic Progenitor Cells. The clonogenic soft agar assay for tumor cells used has been described previously (12). Triplicate cultures were incubated for 14 days at 37° C. in 5% $CO_2$, 5% $O_2$, and 90% $N_2$, and colonies of more than 50 cells were counted in a Zeiss stereo microscope.

The clonogenic capacity of treated and untreated normal progenitor cells was assessed in CFU-GEMM assays (13) in which $5\times10^4$ PBSCs per ml were cultivated individually in standard methylcellulose cultures (HCC-4433 Methocult, Terry Fox Labs, Vancouver, BC) in IMDM medium (GIBCO) After 19 days of incubation, BFU-E and CFU-GM colonies were counted in an inverse phase contrast microscope. Each assay was performed with triplicate cultures in 1 ml 35 mm dishes at 37° C. in a 5% $CO_2$, 100% humidified atmosphere.

Results

Growth of Human Breast Cancer Cells in Soft Agar. In several experiments, a linear relationship between the number of tumor cells seeded and the number of tumor colonies formed was observed. With the PM1 cell line the cloning efficiency was in the range of 20 to 30% (not shown). In experiments with the T-47D and the MCF7 cell lines, the linear relationships previously reported (14) with PEs of 27% and 22%, respectively, were confirmed. These data were used to calculate efficiency of breast cancer cell depletion obtained with the treatment.

Efficacy of Individual and a Mixture of Immunotoxins in Killing Breast Cancer Cells. In model experiments three different concentrations of each IT were used. As demonstrated in Table 4, only marginal effects were obtained with the BM7 conjugate at the two lower concentrations, whereas 2.5 log cell kill was achieved at 1.0 µg/ml close to 3 Furthermore, in the model log cell kill was seen, and at the highest concentration (1 µg/ml) the efficacy was at least 5 logs, the maximal effect possible to assess in this assay (14). With a mixture of both ITs, each at the indicated concentrations, all tumor cells were killed already at 0.1 µg/ml (Table 4). The results show that the mixture of the two ITs can kill the breast cancer cells very efficiently, and the data also suggest that additivity may be obtained by combining the two conjugates. Similar results were obtained when the efficacy of the ITs was tested against the two other breast cancer cell lines (not shown). Because of the expected heterogeneity in antigen expression on target cells, it seemed logical to use the IT combination in the further development of a method suitable for clinical use.

TABLE 4

Efficacy of immunotoxins involving Pseudomonas exotoxin A in killing PM 1 human breast cancer cells.
PM1 cells were incubated with immunotoxins for 2 h at 37° C., seeded out in soft agar, and colony formation was assessed as described in "Materials and Methods".

| ITs with MAbs | Cell line | No. of experiments | Log cell kill[a] immunotoxin concentration of | | |
|---|---|---|---|---|---|
| | | | 0.01 µg/ml Mean[b] ± SD | 0.1 µg/ml Mean ± SD | 1.0 µg/ml Mean ± SD |
| BM7 | PM 1 | 3 | 0.13 ± 0.11 | 0.64 ± 0.15 | 2.55 ± 0.40 |
| | MA 11 | | 0.96 ± 0.18 | 2.02 ± 0.07 | >5 |
| MOC-31 | PM 1 | 3 | 0.81 ± 0.10 | 2.83 ± 0.29 | >5 |
| | MA 11 | | 1.49 ± 0.34 | 2.29 ± 0.07 | >5 |
| BM7\| MOC-31[c] | PM 1 | 4 | 1.16 ± 0.26 | >5 | >5 |
| | MA 11 | | 2.80 ± 0.21 | >5 | >5 |

[a]Calculated from observed number of colonies, taking into account the plating efficiency, and determined as logarithm of the number of cells killed by the treatment.
[b]Mean of the results obtained in independent soft agar experiments, each performed in triplicate.
[c]Each immunotoxin used at the concentration indicated.

Influence of Incubation Time. In the above experiments, a 120 min incubation with ITs was used. In a clinical setting it would, for practical reasons, be advantageous to use an even shorter incubation time. To study whether the time of exposure to the ITs might be reduced without affecting the specific tumor cell kill, the mixture of the two conjugates, used at a concentration of 1 µg/ml of each, was tested with different incubation times against the three breast cancer cell lines. In all cases, the 120 min exposure to the ITs resulted in eradication of all tumor cells. Importantly, the treatment was equally effective when the incubation time was reduced to 90 min and even to 60 min (Table 5), and the data demonstrate that at the IT concentrations used the shortest incubation time is sufficient for killing all clonogenic tumor cells present in the tumor cell cultures.

TABLE 5

Influence of incubation time on the efficacy of a mixture of MOC-31 and BM7 immunotoxins[a] in killing breast cancer cells. Tumor cells alone ($2 \times 10^6$/ml) or admixed (ratio 1:10) to peripheral blood progenitor cells (total $1 \times 10^7$ cells/ml) were incubated with ITs at 37° C. for the indicated periods of time, seeded out in soft agar, and assayed as in Table 4.

| | Mean log tumor cell kill with cell line[b] | | | |
|---|---|---|---|---|
| Incubation time (min) | T-47 D | MCF7 | PM1 | PM1 admixed to PBPCs |
| 60 | >5 | >5 | >5 | >5 |
| 90 | >5 | >5 | >5 | >5 |
| 120 | >5 | >5 | >5 | >5 |

[a]Each IT used at a concentration of 1 µg/ml.
[b]Result obtained in two independent experiments with T-47D and PM1 cells, and in one experiment with MCF7 cell.

To examine whether the toxicity to breast cancer cells might be altered in the presence of a high number of normal hematopoietic cells, experiments were performed in which the tumor cells were admixed at a ratio 1:10 to PBPCs harvested by apharesis. As is demonstrated in Table 5, the ITs killed more than 5 logs of PM1 tumor cells also in the presence of the normal cells, already after an incubation time of only 60 min. Since the results were the same for all three cell lines, the data indicate that the IT procedure may be effectively used in a clinical setting.

Influence of Incubation Conditions and Cell Concentration. To examine the efficacy of the IT procedure under conditions similar to those that would be used on clinical samples, PM1 tumor cells were admixed at a ratio of 1:10 to PBPCs in experiments in which unwashed cells taken directly from the apharesis bag before incubation with the ITs were resuspended in normal saline with ACD (stock solution bag, R2220, Baxter Healthcare Corp., Fenwal Division). The results were compared to those obtained in the initial experiments with cells that were washed and resuspended in RPMI with 10% FCS. It was found (Table 6) that in both cases the treatment with the ITs for 60 min killed all PM1 cells, indicating that for clinical use the ITs can be injected directly into the apharesis bag, and that the low pH under such conditions does not affect the cytotoxicity of the ITs.

TABLE 6

Effect of the incubation conditions on the efficacy of a mixture of MOC-31 and BM7 and immunotoxins in killing PM1 breast cancer cells admixed (ratio 1:10) to peripheral blood progenitor cells isolated by blood cell separator apharesis. Cells from the apharesis bag were put into 3 tubes each containing $1 \times 10^8$ cells. In two tubes, the cells (in volumes of 500–700 µl) were diluted in PBS with 20% ACD and 1% human albumin to a final volume of 1 ml. One of the tubes was used as control and for IT incubation (Group A). The cells in the third tube were washed and resuspended to 1 ml in RPMI with 10% FCS (Group B). In the treatment groups, the cells were incubated at 37° C. for 1 h with 1 µg/ml of each IT, washed and seeded out in soft agar-Assay and calculations as in Table 1. The plating efficiency in the untreated control cultures was in the range of 20%–30%.

| Group | Incubation conditions | No. of experiments | Log tumor cell kill in the presence of different no. of PBPCs | | |
|---|---|---|---|---|---|
| | | | $1 \times 10^7$ | $5 \times 10^7$ | $1 \times 10^8$ |
| A | Unwashed cells treated in normal saline with ACD | 2 | >5 | >5 | >5 |
| B | Cells washed and treated in RPMI with 10% FCS | 2 | >5 | >5 | >5 |

In the apharesis bag the total number of cells will be quite high, and it was conceivable that at such high cell concentrations the efficacy of the procedure might be reduced compared to the conditions used in the model studies. However in experiments where this possibility was tested no difference in efficacy was observed when the total concentration of cells was increased first from $1 \times 10^7$ to $5 \times 10^7$, and then to $1 \times 10^8$ per ml (Table 6).

Toxicity of the ITs to Normal Hematopoietic Progenitor Cells. The effect of the ITs on the survival of CFU-GM and BFU-E was studied under incubation conditions as described above. It was found (Table 7) that even a 120 min incubation of the nucleated PBPCs with the IT mixture did not reduce the survival of the progenitor cells, whether tested after washing and resuspending the cells in RPMI with 10% FCS, or when unwashed cells resuspended in normal saline with ACD were used.

Since in a clinical setting the treated cells will be frozen and thawed before given back to the patient, the effect of such procedures on the progenitor cells was also studied. It was found that the freezing and thawing only slightly reduced the number of CFU-GM and BFU-E (Table 7). Notably, the IT treatment itself did not significantly reduce the survival of the progenitor cells, although a slight reduction in the mean number of cell colonies was seen in the group where the cells had been treated under low pH conditions. The data demonstrate that the concentration of ITs that effectively eradicate the tumor cells after 60 min incubation have only insignificant effect on the survival of normal clonogenic cells treated twice as long.

TABLE 7

Toxicity of a mixture of MOC-31 and BM7 immunotoxins to CFU-GM and BFU-E in fresh human PBPCs harvested after mobilization with G-CSF. Effect of incubation conditions and the freezing procedure. Control and treatment groups as in Table 6. Nucleated PBPCs were incubated with 1 µg/ml of each of the ITs for 2 h at 37° C. before being seeded out ($5 \times 10^4$ cells/dish) in the assay as described in "Materials and Methods".

| | Number of colonies[a] (% of untreated control) | | | |
|---|---|---|---|---|
| | CFU-GM | | BFU-E | |
| Incubation conditions | Before freezing | After freezing | Before freezing | After freezing |
| Untreated | 118 ± 6 (100) | 102 ± 11 (86) | 170 ± 15 (100) | 166 ± 56 (98) |
| Unwashed cells treated in normal saline with 20% ACD | 145 ± 23 (123) | 86 ± 28 (73) | 194 ± 13 (114) | 120 ± 42 (71) |
| Cells washed and treated in RPMI with 10% FCS | 125 ± 25 (106) | 112 ± 16 (95) | 193 ± 73 (114) | 159 ± 74 (94) |

[a]Mean ± SD of results obtained from triplicate cultures in two individual experiments Discussion Autologous transplantation of circulating hematopoietic stem cells has recently attracted considerable interest because of its advantages compared to BM transplantation (15, 16). In addition to rapid reconstitution of bone marrow function, it has been supposed that the use of PBSCs might remove the risk of reinfusing tumor cells contaminating the transplant. However, it has been shown that the problem of tumor cell contamination is reduced but not eliminated (4). It should also be noted that high dose chemotherapy involving the use of colony-stimulating factors may recruit tumor cells into the peripheral blood (7, 8). Therefore, a rapid and practical procedure for purging apharesis products is highly warrented.

Several methods for removing breast cancer cells from BM have been reported, including chemo-immunoseparation, immunomagnetic procedures, and the use of immunotoxins (14, 17, 18, 19). In contrast, only very few studies on purging PBSC preparations have been described (20, 21), but ITs prepared with a ribosome-inactivating protein (22, 23) have been used for killing lymphoid tumor cells added to CD34-positive cell collections prepared from BM (24). In the latter study, a purging efficacy of 2 logs was obtained in addition to the 3 logs indirect purification achieved by the CD34 selection procedure. The objective of the present study was to develop a safe IT procedure to purge breast cancer cells from PBSCs. The results obtained in model experiments demonstrate that 60 min incubation with 1 µg/ml of each of 2 conjugates involving anti-carcinoma antibodies and PE, efficiently killed all tumor cells admixed to PBSCs without toxicity to the normal progenitor cells. Importantly, the method allows the ITs to be added directly to the apharesis product, and after incubation the cells are washed, centrifuged and ready for freezing. Particularly because of its simplicity and efficacy the method should be attractive for use in the management of selected groups of breast cancer patients in conjunction with high dose chemotherapy combined with transplantation of PBSCs. The high selective efficacy of our procedure might be ascribed to the following factors:

First, the antigen recognized by the MOC31 antibody is known to be expressed on most cells in almost all breast cancer specimens examined (10). Also the BM7 antibody, which recognises the core protein expressed by the MUC-1 gene (9), binds to a high fraction of breast cancer cells (25). Together, these two monoclonals seem to cover, to a reasonable extent, the heterogeneity in antigen expression found in breast cancer. Secondly, we have previously demonstrated that when constructing ITs it is important to use a toxin that matches the antibodies used (11). We have found that PE conjugates involving a number of monoclonals, including those that were used here, are very effective (14). Moreover, ITs with PE are always more toxic than equimolar concentrations of free PE (11, 18), demonstrating the specificity of such ITs.

Purging procedures need to be efficient and safe, and it is also necessary that the method is practical and can be used on a clinical scale. In addition to the advantage that the ITs can be added directly to the apharesis bag, our method includes only 60 min incubation time for killing all the clonogenic tumor cells. Moreover, this treatment is not toxic to the normal hematopoietic progenitor cells, and in BM purging experiments even much higher IT concentrations were well tolerated (14). We have also shown that freezing and thawing of the PBSCs treated with the ITs caused no additional toxicity, and it is noteworthy that the IT procedure does not involve the unspecific cell loss that might be experienced with methods involving removal of tumor cells with immunobeads or immunoadsorption.

We have previously calculated the amount of conjugate remaining in IT-treated BM after washing to be about 0.75% of the total amount added (26). In a clinical setting, treatment of PBSCs, containing approximately $2 \times 10^{10}$ mononuclear cells, with the recommended concentration of 2 µg IT/ml ($1 \times 10^8$ cells), would then be expected to result in a maximum of 3 µg IT in the final product. This represents 100–150 times less free toxin than a theoretically calculated maximum tolerable dose (26). Thus, reinfusion of the purged PBSCs would not be expected to give any systemic toxicity.

The success of failure of high dose therapy combined with autologous hematopoietic progenitor cell transplantation may depend even more on the efficacy of the systemic treatment than the efficiency of purging the grafts (1). Nevertheless, it is logical to remove cancer cells that might be present in the autograft, and recent evidence from studies of other tumor types demonstrates the importance of purging (16). In breast cancer, we suggest employing a simple, safe and effective procedure as the one described here.

EXAMPLE 2

Since breast cancer cells may show different sensitivity to immunotoxins, such that the purging activity of BM7 and MOC31 may be different on breast cancer cells from different patients, the same experiment as previously performed with PM1 breast cancer cells (Example 1) was repeated with another cell line, MA11. It was found that the effect of the immunotoxin treatment was as good, or even better, against the MA11 cells compared to PM1 celles (Table 4). the results confirm the high specific activity of the immunotoxin purging treatment.

In separate experiments the kinetics of the cell killing activity of the immunotoxin was studied in an experiment where PM1 breast cancer cells were added to peripheral blood progenitor cells (ratio 1:100). After incubation for two hours, the mixed cell suspension was frozen and thereafter than before the cells were seeded out and the viability of cancer cells and normal progenitor cells assessed in parallel experiments. It was found that intoxication of the breast cancer cells occured rapidly, and within approx. 72 hours all tumor cells were dead. In comparison, no difference in viability of the normal blood progenitor was found in cultures of immunotoxin-treated and non-treated cells within the same time frame.

EXAMPLES 3–4

Carcinoma cells that spread to bone or bone marrow, to pleural and abdominal cavities, to brain and spinal cord tissue, and to the urogenital tract can be selectively killed by immunotoxins administered into the tumor, into said body fluids, or systemically, e.g. to target metastatic tumor cells in tissues such as blood, bone and bone marrow.

EXAMPLE 3

MA-11 human breast cancer cells were injected into the left cardiac ventricle of immunodeficient rats. Untreated control animals developed symptoms of spinal cord compression and had to be killed 34–37 days after cell injection. Animals treated intravenously with a single dose of MOC31-PE (20 μg/rat) showed a prolonged symptom-free survival and some of the animals lived for more than 50 days.

Another experiment in the same model confirmed the results, and in this case some of the animals survived throughout an observation time of 110 days. In these experiments, one group of rats was treated with an immunotoxin consisting of the 425.3 antibody directed against the EGF-receptor conjugated to PE. All the animals in this group survived.

In a third experiment in this model, the control rats showed symptoms of cord compression and had to be killed between day 40 and 60 after cell injection. In this experiment three treatment groups were included, one with 20 μg 425.3-PE, and one receiving 10 mg catch of the two immunotoxins. Significant prolongation of disease-free survival was obtained with both immunotoxins used individually, giving 60% and 80% long term survival with MOC31-PE and 425.3-PE, respectively. In the combination experiments all animals survived disease-free.

In a fourth experiment in this model the effect of MOC31-PE was compared to those of cis-platin and doxorubicin. In this experiment all the MOC31-PE treated animals survived for more than 70 days, whereas doxorubicin only showed a marginal effect, and cis-platin-treated rats did not live longer than the saline-treated control animals. These data convincingly demonstrate that the immunotoxins used are highly superior in killing breast cancer metastases than doxorubicin and cis-platin, two of the most commonly used drugs in the clinic.

EXAMPLE 4

The human breast cancer cell line MT-1 was used in two different experiments. In the first of these, cells were injected into the left cardiac ventricle and the control animals had to be killed because of symptoms of spinal cord compression after a median time of 19 days. Animals treated with 425.3-PE intravenously one day after cell injection all survived. In the other experiments the MT-1 tumor cells were injected directly into the bone marrow cavity of the rat tibia. All untreated animals had to be sacrificed 20 days later because of growing tibial tumors, whereas rats treated with 20 μg of 425.3-PE intravenously one day after cell injection all survived for more than 100 days.

Furthermore, in the model where MT-1 tumor cells were injected directly into the bone marrow of rat tibia the effect of BM7-PE administered either on day 1 or on day 7 was compared to the effects of 425.3-PE, in groups of animals treated on the same days as for BM7-PE. Morover, the effect of doxorubicin (Adriamycin) given intravenously on day 7 and day 14 was also studied. It was found that both immunotoxins cured 80% of the rats, whether administered on day 1 or on day 7. When half the concentrations of each immunotoxin was combined all animals survived. In comparison, doxorubicin was clearly less effective, leaving only 35% of the animals alive after 90 days. The control animals had to be sacrificed 20 days after injection of the cells, as in previous experiments. The data confirm the effect of 425.3-PE previously shown. Importantly, BM7-PE was found to be equally effective as 425.3-PE. Both agents were clearly superior in efficacy compared to doxorubicin, one of the clinical drugs most frequently used against breast cancer. Moreover, the combination of the two immunotoxins cured all animals of their disease.

EXAMPLE 5

In two sets of experiments the effect of a recombinantly produced immuntoxin directed against the erbB2-gene product, and with a recombinantly made variant of PE, was tested. In the model described in example 4 the highest concentration of the recombinant immunotoxin significantly prolonged the lifespan of the animals, and 35% of the rats survived. In a model where the MT-1 breast cancer cells were injected intrathecally in immunodeficient rats, the treatment with the recombinant immunotoxin also given intrathecally (on days 1, 2, and 3) resulted in a significant prolongation in lifespan of the animals. This effect was dose dependent, and the two different doses increased the lifespan of the animals from 10, 6 days (saline-treated controls) to 23, 4 days and 32, 8 days with two different doses of the immuntoxin. At the highest dose 20% of th rats survived. Since no toxicity was observed even with the highest immunotoxin dose, it is expected that the effect at optimal doses may be even better.

REFERENCE

1. Peters, W. P., Ross, M., Vredenburgh, J. J., Meisenberg, B., Marks, L. B., Winer, E., Kurtzberg, J., Bast, R. C. J., Jones, R., Shpall, E., Wu, K., Rosner, G., Gilbert, C., Mathias, B., Coniglio, D., Petros, W., Henderson, I. C., Norton, L., Weiss, R. B., Budman, D., and Hurd, D. High-dose chemotherapy and autologous bone marrow support as consolidation after standard-dose adjuvant therapy for high risk primary breast cancer. J. Clin. Oncol., 11:1132–1143, 1993.
2. Armitage, J. O. Bone marrow transplantation. N. Eng. J. Med., 330:827–838, 1994.
3. Moss, T. J., Sanders, D. C., Lasky, L. C., and Bostrom, B. Contamination of peripheral blood stem cell harvests by circulating neuroblastoma cells. Blood, 76: 1879–1883, 1990.
4. Ross, A. A., Cooper, B. W., Lazarus, H. M., Mackay, W., Moss, T. J., Ciobanu, N., Tallman, M. S., Kennedy, M. J., Davidson, N. E., Sweet, D., and et al. Detection and viability of tumor cells in peripheral blood stem cell collections from breast cancer patients using immunocytochemical and clonogenic assay techniques. Blood, 82: 2605–2610, 1993.
5. Brenner, M. K., Rill, D. R., Moen, R. C., Krance, R. A., Mirro, J., Jr., Anderson, W. F., and Ihle, J. N. Gene-marking, to trace origin of relapse after autologous bone-marrow transplantation. Lancet, 341: 85–86, 1993.
6. Gribben, J. G., Freedman, A. S., Neuberg, D., Roy, D. C., Blake, K. W., Woo, S. D., Grossbard, M. L., Rabinowe, S. N., Coral, F., Freeman, G. J., and et al. Immunologic purging of marrow assessed by PCR before autologous bone marrow transplantation for B-cell lymphoma. N. Engl. J. Med., 3 25: 1525–1533, 1991.
7. Shpall, B. J., and Jones. R. B. Release of tumor cells from bone marrow. Blood, 83: 623–625, 1994.
8. Brugger, W., Bross, K. J., Glatt, M., Weber, F., Mertelsmann, R., and Kanz, L. Mobilization of tumor cells and hematopoietic progenitor cells into peripheral blood of patients with solid tumors. Blood, 83: 636–640, 1994.
9. Strous, G. J., and Dekker, J. Mucin-type glycoproteins. Crit. Rev. Biochem. Molecu. Biol., 27: 57–92, 1992.
10. Leij, L. D., Postmus, P. E., Poppema, S., Elema, J. D., and The, T. H. The use of monoclonal antibodies for the pathological diagnosis of lung cancer. In: H. H. Hansen (ed), Lung Cancer: Basic and Clinical Aspects,. pp. 31–48. Boston: Martinus Niijhoff Publishers, 1986.
11. Godal, A., Kumle, B., Pihl, A., Juell, S., and Fodstad, Ø. Immunotoxins directed against the high-molecular-weight melanoma-associated antigen. Identification of potent antibody-toxin combinations. Int. J. Cancer, 52: 631-635, 1992.
12. Courtenay, V. D. and Mills, J. An in vitro colony assay for human tumorus grown in immune-suppressed mice and treated in vivo with cytotoxic agents. Br. J. Cancer, 37: 261–268, 1978.
13. Wang, M. Y., Kvalheim, G., KvalØy, S., Beiske, K., Jakobsen, E., Wijdens, J., Pihl, A., & Fodstad, Ø. An effective immunomagnetic method for bone marrow purging in T cell malignancies. Bone Marrow Transplant., 9: 319-323, 1992.
14. Myklebust, A. T., Godal, A., Juell, S., Pharo, A., and Fodstad, Ø. Comparison of two antibody-based methods for elimination of breast cancer cells from human bone marrow. Cancer Res., 54: 209–214, 1994.
15. Eaves, C. J. Peripheral blood stem cells reach new heights. Blood, 82: 1957-1959, 1993.
16. Shpall, E. J., Jones, R. B., Bearman, S. I., Franklin, W. A., Archer, P. G., Curiel, T., Bitter, M., Claman, H. N., Stemmer, S. M., Purdy, M., Myers, S. E., Hami, L., Taffs, S., Heimfeld, S., Hallagan, J., and Berenson, J. Transplantation of enriched CD34-positive autologous marrow into breast cancer patients following high-dose chemotherapy: Influence of CD34-positive peripheral-blood progenitors and growth factor on engraftment. J. Clin. Oncol., 12: 28–36, 1994.
17. Bjorn, M. J., Groetsema, G., and Scalapino, L. Antibody-Pseudomonas exotoxin A conjugates cvtotoxic to human breast cancer cells in vitro. Cancer Res., 46: 3262–3267, 1986.
18. Anderson, I. C., Shpall, E. J., Leslie, D. S., Nustad, K., Ugelstad, J., Peters. W. P., and Bast, R. C. Jr. Elimination of malignant clonogenic breast cancer cells from human bone marrow. Cancer Res., 49: 4659–4664, 1989.
19. O'Briant, K. C., Shpall, E. J., Houston, L. L., Peters, W. P., Bast, R. C. Jr. Elimination of conogenic breast cancer cells from human bone marrow: A comparison of immunotoxin treatment with chemoimmunoseparation using 4-hydroperoxycyclophamide, monoclonal antibodies, and magnetic microspheres. Cancer. 68: 1272–1278, 1991.
20. Stray, K. M., Corpuz, D., Colter, K. M., Berenson, R., and Heimfeld, S. Purging tumor cells from bone marrow or peripheral blood using avidin biotin immunoadsorptioin. In: P. G. Adrian. G. Samuel, and A. W—W. Diana (eds.), Advances in bone marrow purging and processing, pp. 97–103. Orlando: Wiley-Liss, Inc., 1994.
21. Tyer, C. L., Vredenburgh, J. J., Heimer, M., Bast, R. C. Jr., and Peters, W. P. Breast cancer cells are effectively purged from peripheral blood progenitor cells using an immunomagnetic technique. Abstract to First meeting of International Society for Hematotherapy and Graft Engineering, Orlando, Fla., 1993.
22. Stirpe, F., Barbieri, L., Battelli, M. G., Soria, M., and Lappi, D. A. Ribosome-inactivating protein from plants: present status and future prospects. Bio/Technology 10: 405–412, 1992.
23. Barbieri, L., Battelli, M. G., Stirpe, F. Ribosome-inactivating protein from plants. Biochem. Biophys. Acta. 1154: 237–282, 1993.
24. Lemoli, R. M., Tazzari, P. L., Fortuna, A., Bolognesi, A., Gulati, S. C., Stirpe, F., and Tura, S. positive selection of hematopoietic $CD34^+$ stem cells provides 'indirecte purging' of cd34-lymphoid cells and the purging efficiency is increased by anti-CD2 and CD30 immunotoxins. Bone Marrow Transplant., 13: 465–471, 1994.
25. Diel, I. J., Kaufmann, M., Goemer, R., Costa, S. D., Kaul, S., and Bastert, G. Detection of tumor cells in bone marrow of patients with primary breast cancer: a prognostic factor for distant metastasis. J. Clin. Oncol., 10: 1534-1539, 1992.
26. Myklebust, A. T., Godal, A., Pharo, A., Juell, S., and Fodstad, Ø. Eradication of small cell lung cancer cells from human bone marrow with immunotoxins. Cancer Res., 53: 3784–3788, 1993.

What is claimed is:

1. Method to kill breast cancer cells expressing EGP2 and MUC1 antigens in a cell population selected from the group consisting of cells comprising nucleated cells in peripheral blood and bone marrow cells comprising $CD-34^+$ cells selected from the above nucleated cells, the method comprising:

incubating the cell population with a combination of two or more immunotoxins, wherein each immunotoxin comprises a conjugate between an antibody or antigen binding fragment thereof and a cell toxin or active toxin fragments, or a recombinantly produced antibody or antigen binding antibody fragments, further comprising toxins or active toxin fragments, wherein the antibodies or antigen binding fragment thereof are directed to epitopes on the antigen EGP2 expressed by the gene GA733-2 and to epitopes on the antigen expressed by the MUC1 gene and the toxin is Pseudomonas exotoxin A, wherein the antibodies are selected from the group consisting of MOC31, BM2, antibodies binding to the same epitopes as MOC31 or BM2, or antigen binding fragments thereof.

2. The method according to claim 1, wherein the antibodies are MOC31 and BM2, or antigen binding fragments thereof.

3. The method according to claim 1 wherein said incubating consists of administering the immunotoxins in vivo.

4. The method according to claim 3, wherein the immunotoxins are administered systemically.

5. The method according to claim 3, the wherein the immunotoxins are administered directly into a tumor or intrapleurally intra-abdominally.

6. The method of claim 1, wherein said incubating consists of administering the immunotoxins *ex vivo*.

7. A method for killing breast cancer cells expressing EGP2 and MUC1 antigens in a cell population comprising nucleated peripheral blood cells or bone marrow cells, the method comprising obtaining the population of cells that contains rho breast cancer cells;
   contacting the population of cells ex vivo with two or more immunotoxins, wherein a first immunotoxin comprises a PE molecule conjugated to an antibody or an antibody fragment capable of binding an EGP2 antigen which is expressed by a GA733-2 gene and a second immunotoxin comprising a PE molecule conjugated to an antibody or an antibody fragment capable of binding an antigen encoded by the MUC1, gene,
   wherein the first immunotoxin comprises a PE molecule conjugated to a MOC31 antibody, an antibody binding to the same epitope as MOC31, or an antigen-binding fragment thereof, and the second immunotoxin comprises a PE molecule conjugated to a BM2 antibody, an antibody binding to the same epitope as BM2, or an antigen-binding fragment thereof.

8. The method according to claim 7 wherein the first immunotoxin comprises a PE molecule conjugated to a MOC31 antibody or an antigen-binding antibody fragment thereof, and the second immunotoxin comprises a PE molecule conjugated to a BM2 antibody or an antigen-binding antibody fragment thereof.

9. The method according to claim 8 wherein the cell population is obtained from a cancer patient.

10. The method according to claim 10 wherein the cell population comprises $CD34^{30}$ cells.

11. The method according to claim 10 wherein the cell population is enriched or positively selected for CD34+ cells.

12. The method according to claim 1 wherein treatment of the cell population with the two or more immunotoxins causes toxicity to breast cancer cells and is not toxic to CD34+ cells in the population.

13. A method for killing breast cancer cells expressing EOP2 and MUC1 antigens in a patient, the method comprising
   administering to the patient a therapeutically effective amount of two or more immunotoxins, wherein a first immunotoxin comprises a PE molecule conjugated to an antibody or an antibody fragment capable of binding an EGP2 antigen which is expressed by a GA733-2 gene and a second immunotoxin comprises a PE molecule conjugated to an antibody or an antibody fragment capable of binding an antigen encoded by the MUTC1, genes,
   wherein the first immunotoxin comprises a PE molecule conjugated to a MOC31 antibody, an antibody binding to the same epitope as MOC31, or antigen-binding fragment thereof, and the second immunotoxin comprises a PE molecule conjugated to a BM2 antibody, an antibody binding to the same epitope as BM2, or an antigen-binding fragment thereof.

14. The method according to claim 4 wherein the immunotoxins are administered systemically to kill malignant cells.

15. The method according to claim 14 wherein the malignant cells have spread to blood or bone marrow.

16. Method to kill breast cancer cells or other carcinoma cells expressing the same target antigens in a cell population selected from the group consisting of cells comprising nucleated cells in peripheral blood and bone marrow cells comprising $CD-34^{30}$ cells selected from the above nucleated cells, the method comprising:
   incubating the cell population with a combination of two or more immununotoxins, wherein each immunotoxm comprises a conjugate between an antibody or antigen binding fragments and a cell toxin or active toxin fragments, or a recombinantly produced antibody or antigen binding fragments, further comprising toxins or active toxin fragments, wherein the antibodies or antigen binding fragments are directed to epitopes on the antigen EGP2 expressed by the gene GA733-2 and to epitopes on the antigen expressed by the MUC1 gene and the toxin is Pseudomonas exotoxin A, wherein the antibodies are selected from the group consisting of MOC31, BM7, antibodies binding to the same epitopes as MOC31 or BM7, or antigen binding fragments thereof.

17. A method for killing breast cancer cells expressing EGP2 and MUC1 antigens in a cell population comprising nucleated peripheral blood cells or bone marrow cells, the method comprising
   obtaining the population of cells that contains the breast cancer cells
   contacting the population of cells *ex viva* with two or more immunotoxins, wherein a first immunotoxin comprises a PE molecule conjugated to an antibody or an antibody fragment capable of binding an EGP2 antigen which is expressed by a GA733-2 gene and a second immunotoxin comprising a PE molecule conjugated to an antibody or an antibody fragment capable of binding an antigen encoded by the MUC, 1, gene,
   wherein the first immunotoxin comprises a PE molecule conjugated to a MOC31 antibody, an antibody binding to the same epitope as MOC31, or an antigen-binding antibody fragment thereof, and the second immunotoxin comprises a PE molecule conjugated to a BM7 antibody, an antibody binding to the same epitope as BM7, or an antigen-binding fragment thereof.

18. The method according to claim 16, wherein the antibodies are MOC3 and BM7, or antigen binding fragments thereof.

19. The method according to claim 17, wherein the first immunotoxin comprises a PE molecule conjugated to a MOC31 antibody or an antigen-binding fragment thereof, and the second immnunotoxin comprises a PE molecule conjugated to a BM7 antibody or an antigen-binding fragment thereof.

* * * * *